United States Patent [19]

Volk

[11] Patent Number: 5,255,025
[45] Date of Patent: Oct. 19, 1993

[54] MEASUREMENT APPARATUS FOR INDIRECT OPHTHALMOSCOPY

[76] Inventor: Donald A. Volk, 9378 Jackson Ave., Mentor, Ohio 44060

[21] Appl. No.: 776,063

[22] Filed: Oct. 15, 1991

[51] Int. Cl.⁵ ............................................... A61B 3/10
[52] U.S. Cl. ..................................... 351/205; 351/219
[58] Field of Search .......... 351/205, 214, 219, 160 R, 351/245; 359/708, 379

[56] References Cited

U.S. PATENT DOCUMENTS 4,307,944 12/1981 Schirmer ......................... 351/205 X
4,721,378 1/1988 Volk ..................................... 351/205

Primary Examiner—Rodney B. Bovernick
Attorney, Agent, or Firm—Oldham, Oldham, & Wilson Co.

[57] ABSTRACT

A measurement apparatus designed to be used in association with the housing supporting an indirect ophthalmoscopy optical system is shown. The optical system may include one or more lens elements contributing to the formation of an aerial fundus image. Exact positioning of the lens elements as well as consistent lens housing dimensions insure accurate location of the aerial image relative to an examined eye. Such positioning may be accomplished by means of a contact lens of given thickness and power, in predetermined relationship with the image forming lens(es), or by means of an adapter positioned on the external eyelid of a patient, with the image forming lens(es) supported therein. A reticle is formed on a transparent disc of glass or other material, and is fitted into a supporting structure which is adapted to be selectively retained in association with the housing of the indirect ophthalmoscopy optical system. The reticle may be manually positioned at a location which coincides with the formed aerial image of the optical system, thus allowing quantitative measurement of interior portions of the eye as represented in the aerial image. The position of the supporting structure for the reticle is adjustable to accommodate for any shifting of the image plane created by specific refractive conditions of the examined eye.

15 Claims, 3 Drawing Sheets

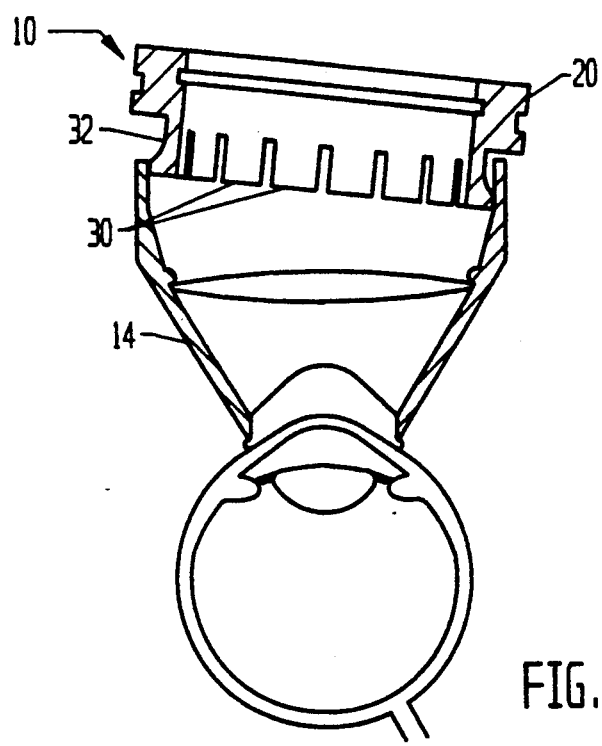
FIG. 6
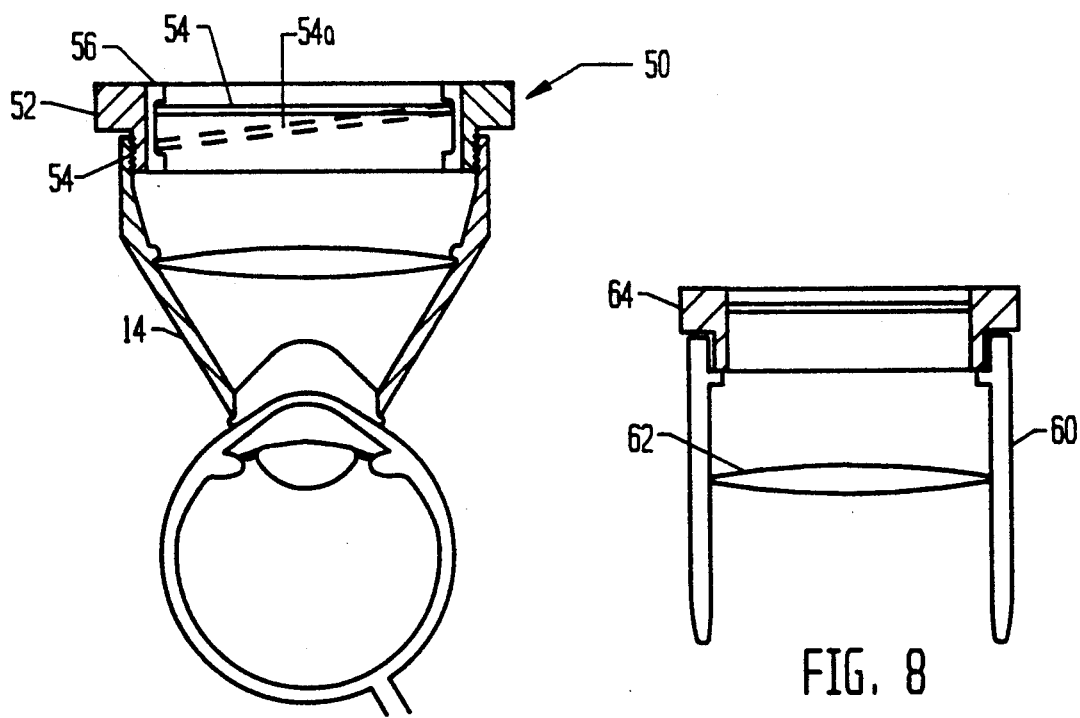
FIG. 7
FIG. 8

MEASUREMENT APPARATUS FOR INDIRECT OPHTHALMOSCOPY

FIELD OF THE INVENTION

This invention generally relates to an apparatus to be used in association with indirect ophthalmoscopy for the indirect measurement of portions or areas of the eye fundus such as for instance, such as for instance, in biomicroscopy of the eye. More particularly, the invention relates to a measurement apparatus forming part of an indirect ophthalmoscopy lens device or accessory used therewith which includes a disc reticle. The disc reticle is selectively positioned to be coincident with the image plane or portions of the formed image as produced by the lens system. Measurement of various structures viewed in the fundus image may then be performed for diagnostic and evaluative analysis of any retinal abnormalities.

BACKGROUND OF THE INVENTION

Indirect ophthalmoscopy is recognized as an important technique in diagnostic and evaluative examination of the central and peripheral retina and related structures of the eye. Degenerative retinal diseases may be quantitatively evaluated by tonometry, visual field analysis and other techniques, but may be subject to various limitations and possible errors. Other techniques using complex photographic analysis or computer analysis have been used to determine the size and dimensions of internal eye structures. These methods as well help to provide valuable information relating to retinal health, but require expensive equipment and are often time consuming and complicated. As the retina and associated structures are readily examined using indirect ophthalmoscopy techniques, the possibility of utilizing indirect ophthalmoscopy in topographic evaluations of the size and shape of the central and peripheral retina and related structures is becoming increasingly important. For example, detectable changes in the optic nerve head may reflect the loss of retinal ganglion cell axons, which has been found to occur at early stages in glaucoma. Similarly, dimensional variations in the neuroretinal rim and optic disc have been correlated with parameters of visual function and with assessments of the retinal nerve fiber layer in glaucoma diagnosis. Precise measurements of the neuroretinal rim, optic disc and associated structures may therefore facilitate examination and diagnosis of diseases in the central and peripheral retina.

In indirect ophthalmoscopy, examination of the fundus of the eye by the observation of a real aerial fundus image is performed. The observation of the aerial image of the fundus is performed using either a binocular slit lamp biomicroscope or binocular indirect ophthalmoscope. To generate the real aerial image of the fundus, various optical systems have been developed. For example, in U.S. Pat. No. 4,738,521, an optical lens for indirect ophthalmoscopy is described, wherein an objective lens is used as a condensing lens acting to converge the light from an ophthalmoscope or biomicroscope light source to the entrance pupil of the eye so as to illuminate the eye fundus and also as an image forming lens adapted to form an aerial image of the fundus to be viewed by an examiner. Such an optical system may be provided as a hand-held indirect ophthalmoscopy lens. Other examples of indirect ophthalmoscopy lenses and optical systems are shown in U.S. Pat. Nos. 4,721,378 and 4,627,694. In such hand-held devices of this type, a real, inverted and magnified image of the retina is formed in space at approximately the front focus of the condensing lens in the optical system. Generally, the position of the image as produced by the indirect ophthalmoscopy optical system is not immediately apparent to the examiner, and the indirect ophthalmoscope or slit lamp biomicroscope is adjusted so as to provide a clear fundus image. In the unaccomodated emmetropic eye, light rays emerging from the eye are parallel, and the size of the formed aerial image is dependent on lens position and power. On the other hand, any refractive error in the examined eye will result in a shifting in the position of the image plane.

More recently, other hand-held indirect ophthalmoscopy lens systems have been developed, which include one or more anterior lens elements used in conjunction with a contact element. In that the lens system is positioned directly on the cornea of the examined eye, the position the aerial image in relation to lens and examined eye remains generally constant. An example of such an indirect ophthalmoscopy optical device is shown in U.S. Pat. No. 5,046,836. Further, an adaptor for a lens retaining ring and associated indirect ophthalmoscopy lens as seen in U.S. Pat. No. 4,913,545, also acts to properly space the indirect ophthalmoscopy lens mounted therein at a predetermined distance from the examination lens and eye of the patient. In these systems, the image forming lens is positioned at a predetermined and constant location relative to the examined eye. Likewise, for a particular lens power and design, the front and back focus of the lens is known, and the position of the aerial image as formed by the lens system may also be known.

SUMMARY OF THE INVENTION

Based upon the foregoing, there has been found a need to provide a measuring apparatus for use with an indirect ophthalmoscopy optical system which will allow quantitative measurements of the central and peripheral retina and associated structures of the eye. It is therefore a main object of the invention to provide a measurement apparatus which may be integrally formed with an indirect ophthalmoscopy optical system or may be provided as an accessory to allow precise measurement of the retinal structures.

Another object of the invention is to provide a measuring apparatus for use with an indirect ophthalmoscopy optical system, wherein the measurement apparatus is axially and angularly adjustable to allow for variations in the axial position of a formed fundus image as well as to accommodate for curvature and variations in the formed image.

A further object of the invention is to provide a measurement apparatus for use in indirect ophthalmoscopy, wherein the apparatus is readily attachable to and removable from a hand-held housing associated with the indirect ophthalmoscopy optical system.

A further object of the invention is to provide a measurement apparatus for use in indirect ophthalmoscopy, wherein the measurement apparatus may be selectively positioned in or removed from the optical system, and various reticles may be selectively used in the apparatus.

The measurement apparatus of the invention is designed to be used in association with the housing supporting an indirect ophthalmoscopy optical system. The system may include one or more lens elements contributing to the formation of the aerial image. Exact positioning of the lens elements as well as consistent lens housing dimensions insure accurate location of the aerial image. Such positioning may be accomplished by means of a contact lens of given thickness and power, in predetermined relationship with the image forming lens(es), or by means of an adapter positioned on the external eyelid of a patient, with the image forming lens(es) supported therein. A reticle is formed on a transparent disc of glass or other material, and is fitted into a supporting structure which is adapted to be selectively retained in association with the housing of the indirect ophthalmoscopy optical system. The reticle may be manually positioned at a location which coincides with the formed aerial image of the optical system, thus allowing quantitative measurement of interior portions of the eye as represented in the aerial image. The position of the supporting structure for the reticle is adjustable to accommodate for any shifting of the image plane created by specific refractive conditions of the examined eye. Additionally, the reticle is angularly adjustable relative to the axis of the image forming lens(es) to compensate for field curvature or other variations, especially in the periphery of the formed image. The reticle and supporting structure may together be provided as a separate accessory or be formed as an integral part of the indirect ophthalmoscopy lens optical system. In either case, the reticle is adapted to be easily removed from the optical system to enable normal diagnostic examination to be performed therewith.

BRIEF DESCRIPTION OF THE DRAWINGS

These and other objects and advantages of the invention will become apparent upon a further reading of the detailed description of preferred embodiments of the invention, in conjunction with the drawings, wherein:

FIG. 6 is an enlarged cross-sectional view showing angular adjustment of the measuring apparatus relative to the image forming lens of the indirect ophthalmoscopy optical system;

FIG. 7 is an enlarged cross-sectional view of an alternate embodiment of the measurement apparatus for use with an indirect ophthalmoscopy system including a contact and image forming lens; and FIG. 8 is an enlarged cross-sectional view of an alternate embodiment of the measurement apparatus for use with an indirect ophthalmoscopy optical system including an image forming lens and adaptor for spacing of the lens from the patient's eye.

DETAILED DESCRIPTION OF THE INVENTION

Figure 1:
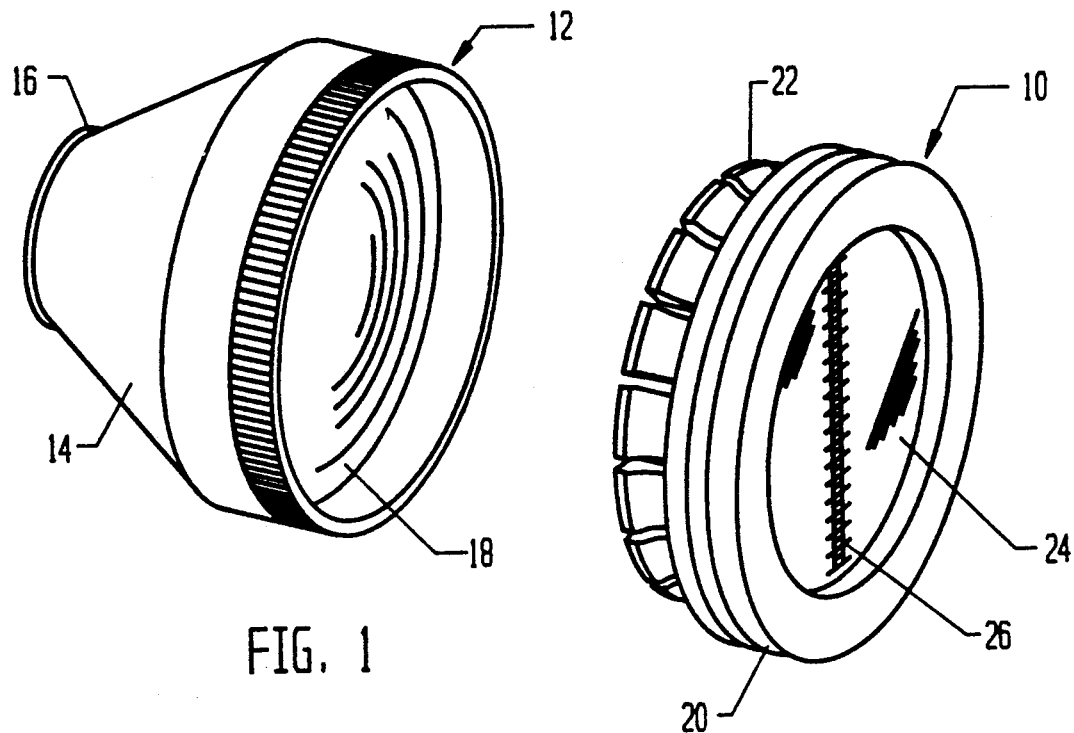
FIG. 1 is an enlarged, perspective view of a detachable measuring apparatus and the indirect ophthalmoscopy optical system with which it is adapted to be used.
Figure 2:
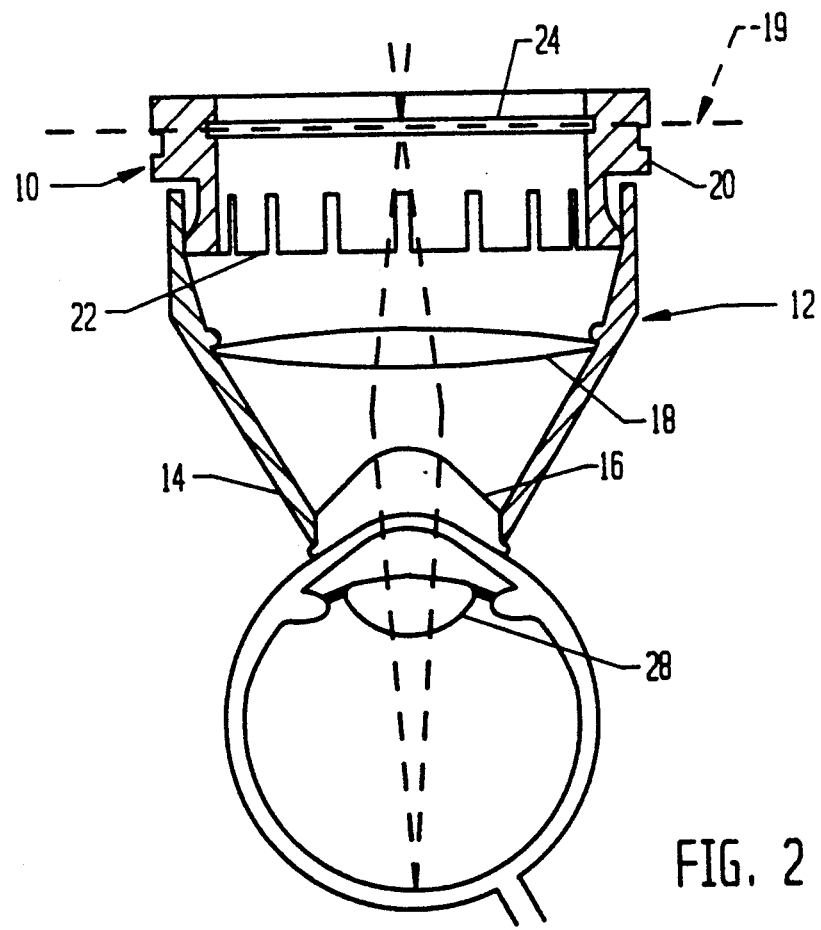
FIG. 2 is a diagrammatic, sectional illustration of the measuring apparatus mounted for use in an indirect ophthalmoscopy lens device and situated against a patient's eye for examination thereof by a practitioner.

Turning now to FIGS. 1 and 2, a first embodiment of the measuring apparatus 10 which is to be used in associated with an indirect ophthalmoscopy optical system 12 to allow measurement of interior structures of an eye. The indirect ophthalmoscopy optical system 12 as shown in this embodiment, comprises a lens housing 14 which supports and retains a contact lens 16 and an image forming lens 18 in a predetermined relationship to one another. The optical system 12 comprises a compound diagnostic indirect ophthalmoscopy lens system, wherein the contact and image forming lenses act in conjunction with one another to produce a wide field of view image of the fundus of an eye as well as to produce a condensing lens system for projection of light from a biomicroscope light source to produce a clear image of the light source aperture on the fundus of the eye. In the arrangement of the indirect ophthalmoscopy optical system 12, to obtain the maximum field of view and desired optical resolution, the lenses of the system are arranged such that in use with an illumination system associated with a slit lamp biomicroscope or ophthalmoscope, the illumination beam waist will be positioned approximately in the pupil of the examined eye to obtain wide illumination of the fundus of the eye. In order to properly position the lenses of the optical system, the contact lens 16, positioned on the anterior corneal surface of the eye, fixes an axial relationship between the contact lens 16 and image forming lens 18 to achieve optimum illumination and visualization through the pupil aperture stop of the examined eye.

In use, the indirect ophthalmoscopy optical system 12 provides a power focal optical system, wherein the focal plane of a biomicroscope or the like is optimally positioned so as to be conjugate with the focal plane of the aperture stop of the illumination system associated therewith. The image forming lens 18 is thus positioned by means of the housing 14, such that the back focus of the combined contact lens/image forming lens(es) is situated at the pupil of the examined eye. Thus, fixing the relationship of the image forming lens 18 relative to the examined eye by means of the contact lens 16 and housing 14, the practitioner can predict the location of the real aerial image of the fundus.

As seen in FIGS. 1-4, the measurement apparatus 10 includes a housing 20, having attachment means 22 associated therewith to allow housing 20 to be retained in a desired relationship with respect to housing 14 of the optical system and the image forming lens 18 thereof. The measurement system 10 also includes a transparent disc 24 on which is provided a reticle 26 for performing quantitative measurements of eye structures. As seen in FIG. 2, the housing 20 of measurement apparatus 10 may be positioned within housing 14 of the optical system in a predetermined relationship, such that the transparent disc 24 is positioned to coincide with the back focal plane of image forming lens 18 and coincident with image plane 19. It should be evident that upon positioning the transparent disc 24 and reticle 26 coincident with image plane 19, measurements of structures in the fundus image in a simple and accurate manner. In a preferred form, the reticle 26 is provided as a micrometer disc reticle having one tenth millimeter divisions corresponding to the magnification characteristics of the indirect ophthalmoscopy optical system. For example, the magnification of an optical system including the contact lens 16, image forming lens 18 and crystalline lens 28 of the examined eye is given by the equation $M=-f_o/f_e$, where $f_o$ is the focal length of the crystalline lens 28 or the anterior focus of the eye, and $f_e$ is the focal length of the combination contact lens 16 and image forming lens 18. For example, in an emmetropic or normal eye, the refractive power is approximately 58.6 diopters. If the combined power of contact lens 16 and image forming lens 18 is 90 diopters for example, the aerial image magnification is calculated to equal approximately 0.65, such that the fundus image will be slightly minified accordingly. For this example, the divisions of reticle 26 may be selected such that a one millimeter division will be equivalent to 0.65 millimeters so as to compensate for the magnification characteristics of the optical system. It should thus be evident that depending upon the qualities of the optical system, the scale of reticle 26 may be adjusted accordingly, such that quantitative measurements of eye structures may be accurately performed.

Figure 3:
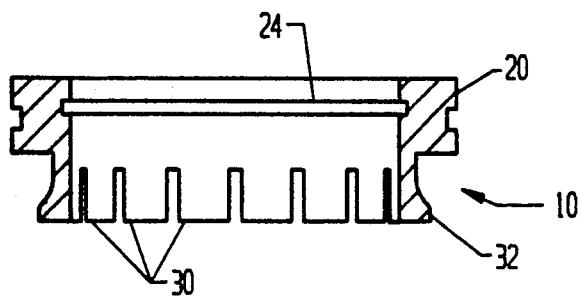
FIG. 3 is an enlarged cross-sectional view of the measurement apparatus in a first embodiment thereof.
Figure 4:
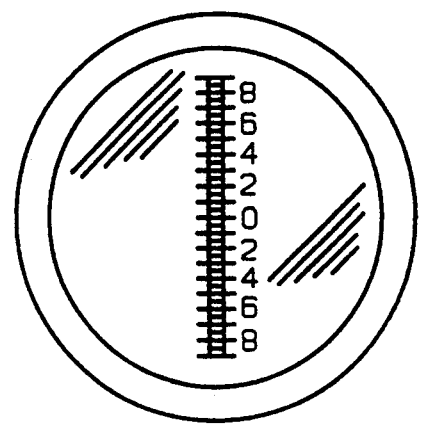
FIG. 4 is an enlarged top elevational view of the embodiment of the measurement apparatus as seen in FIG. 3.

As seen in FIG. 3, the measurement apparatus 10 of this embodiment includes yieldable tabs 30 which extend forwardly from housing 20 and are adapted to be received in snug frictional coupling relation with an interior peripheral surface of a housing in association with an indirect ophthalmoscopy optical system. The housing 20 may be machine or molded from plastic material or the like, with the outwardly extending tabs 30 formed as having a tapered outer surface 32 adapted to engage the optical system housing, wherein tabs 30 will be deflectable inwardly upon being inserted into the optical system housing, and will provide an outwardly directed biasing force acting to retain the measurement apparatus 10 in a desired position relative to housing 14. The transparent disc 24 may be secured on the interior of housing 20 in a slightly recessed position to avoid possible damage thereto, by any suitable means as desired. The housing 20 is adapted to be hand manipulated by the practitioner for use with the indirect ophthalmoscopy optical system, and as shown in FIG. 3, and may be a separate accessory unit associated with a particular optical system. A retaining ring or the like may be provided to secure disc 24 in a desired position while allowing subsequent removal for changing the disc for any desired reason. For example, an alternate reticle may be provided having a different scale or different reticle pattern. for use in examination of the fundus. For example, the prior use of ocular fundus charts which include a series of concentric circles and radiating meridian lines may be provided as the reticle, to more definitively chart the fundus in a topographic evaluation thereof.

Figure 5:
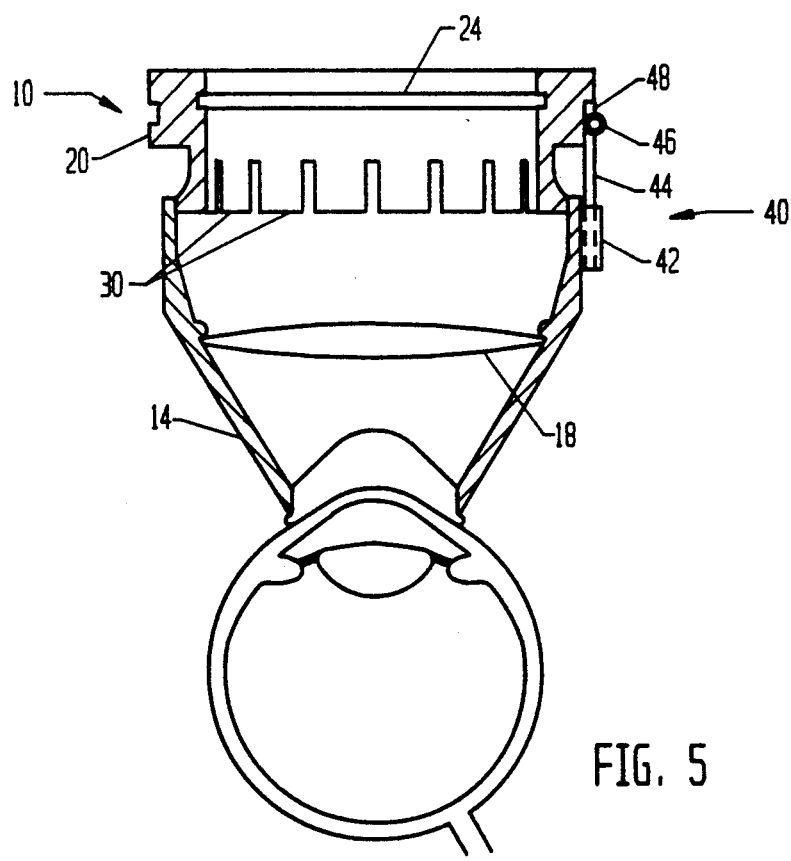
FIG. 5 shows an enlarged cross-sectional view indicating axial adjustment of the measuring apparatus relative to the image forming lens of the indirect ophthalmoscopy optical system.

Turning now to FIG. 5, there is shown a schematic illustration indicating axial adjustment of the measurement apparatus of the invention in an alternate embodiment thereof. As the examined eye departs from emmetropia eye, the refractive error will act to shift the location of the formed aerial image with respect to the image forming lens of the optical system, even though the distance from the eye has not changed. In order to enable measurement of the shifted image, the reticle 26 and transparent disc 24 must be repositioned coincident with the image plane of the optical system as previously described. To account for any shifting of the image plane due to refractive error of the examined eye, axial adjustment of the measurement apparatus 10 is provided. As seen in FIG. 5, the housing 20 may be hand manipulated so as to be withdrawn slightly from a fully seated positioned within housing 14 of the optical system. The outwardly extending yieldable tabs 30 maintain frictional engagement with housing 14 even in such an extended position as desired. In this way, the relative position of transparent disc 24 and the reticle are varied with respect to the position of image forming lens 18 as desired. For a particular optical system with which the measurement apparatus 10 is to be used, the range of axial adjustment from a fully seated position to a fully extended position should account for any shifting of the image plane which may occur due to the normal range of refractive conditions encountered. In this way, the reticle of disc 24 will be brought into view parfocal with the fundus image, thus allowing measurements to be obtained.

Also shown in this embodiment is a hinge assembly 40 which will allow the measurement apparatus 10 to be associated as an integral part of the indirect ophthalmoscopy optical system. The hinge assembly 40 may comprise a standard hinge which will allow the apparatus to be easily removed from the optical path or may be an adjustable hinge assembly. An adjustable hinge is shown to include a retaining housing 42 fixed to housing 14 of the optical system, into which an extending plate member 44 is slidably retained. A hinge 46 is provided in association with member 44 along with an additional plate member 48 secured to housing 20. The hinge 46 allows the housing 20 to be pivoted out of the optical path of the indirect ophthalmoscopy optical system, for conventional diagnostic use of the imaging system. The outwardly extending member 44 additionally allows housing 20 to be axially adjusted as previously described, without impairing the function of the hinge assembly 40.

Turning now to FIG. 6, a schematic illustration of angular adjustment of the measurement apparatus relative to the optical system is shown. Although a generally desired to obtain a planar aerial image of the fundus which is substantially free of optical aberrations, lateral astigmatism and field curvature, the possibility of such disconformities in the formed aerial image is present. Thus, the aerial image formed by the optical system may include field curvature, which is especially apparent at the peripheral regions of the formed image. Portions of the image which depart from a flat field plane may thus inhibit proper measurements from being obtained at such locations. In the present invention, the measurement apparatus is angularly adjustable or tiltable relative to the image forming lens 18 of the optical system, to allow a portion of the reticle to be easily moved into the field plane in which a portion of the image lies. As previously mentioned in this embodiment of the measurement apparatus 10, the outwardly extending yieldable tabs 30 may include the tapered outer surface 32 which allows tilting of housing 20 relative to optical system housing 14. The nature of the outwardly extending tabs 30 also allows defection thereof upon tilting to allow such angular movement while maintaining frictional engagement with housing 14. Any field curvature or departure from a flat field plane will be compensated by the amount of angular tilting allowable in the construction of the measurement apparatus 10, and will facilitate measurement of eye structures even if the formed fundus image departs from a flat field plane.

Another embodiment of the invention is shown in FIG. 7, wherein the measurement apparatus 50 of the invention may again include a housing 52 adapted to support a transparent disc and reticle 54 therein. In this embodiment, the housing 52 may be provided with outer threaded surfaces 54 adapted to engage an internal thread within housing 14 of an indirect ophthalmoscopy optical system. In this way, the housing 52 may be threadably engaged at any desired location relative to housing 14, wherein rotation of housing 52 will facilitate adjustment of the position of disc reticle 54. As previously mentioned, axial adjustment of the position of disc reticle 54 will allow positioning thereof coincident with the image plane of the optical system. Also in this embodiment, there may be provided a retaining ring 56 positioned on the interior of housing 52, which is adapted to support and retain disc reticle 54. The retaining ring 56 allows disc reticle 54 to be tilted relative to housing 52 while retaining it in association therewith as shown in ghost at 54a. Again the axial as well as angular adjustment of the reticle disc 54 by relative movement of housing 52 or disc 54 itself enables measurements of internal eye structures to be performed simply and effectively.

Although the embodiments of the invention have been described in association with an indirect ophthalmoscopy image forming optical system which include a contact lens and an image forming lens adapted to fix the relationship of these lenses with respect to an examined eye, it should be evident that alternate methods of implementation of the measurement system can be achieved. As seen in FIG. 8, a lens positioning device 60, as for instance that shown in U.S. Pat. No. 4,913,545, may be used in conjunction with a single image forming lens 62. In this embodiment, the adaptor 60 includes means for engaging the external eye lids to aid maintaining the engaged eye lids open as well as spacing the image forming lens 62 the desired predetermined distance from the examined eye. As previously mentioned, optimal lens positioning for fundus illumination as well as image forming capabilities is achieved by positioning the illumination beam waist in the pupil aperture of the eye. Such positioning will allow the greatest illumination and visualization of the fundus through the pupil aperture stop. The adaptor 60 may thus be used to readily position the image forming lens 62 a predetermined distance from the eye, so as to enable measurements to be taken on the formed image using the measurement apparatus of the invention. The apparatus as described with reference to FIG. 8 may be in accordance with any of the embodiments of the invention as previously described.

The apparatus of the invention enables measurements to be obtained for internal structures of the eye including the optic disc, neuroretnal rim and cup, lesions or other structures of the eye in a simplified and flexible manner. The measuring apparatus is used tin conjunction with an image forming optical system designed to position an image forming lens a predetermined distance from an examined eye, such that the location and size of a formed image may be calculated and measurement obtained. Although preferred embodiments of the invention have been described, it should be understood that various modifications would be obvious to those skilled in the art, and are embodied within the present invention as defined by the appended claims.

What is claimed is:

1. An apparatus for examination of the fundus of the eye by indirect ophthalmoscopy, comprising,
a housing supporting an optical system having at least one lens, including an imaging lens to form an aerial image of the fundus of the examined eye, wherein said housing is located relative to said examined eye such that said image forming lens is positioned a distance from the eye to form said aerial image,
a reticle formed on a transparent disc of material, and a supporting means for said transparent disc of material including outwardly extending yieldable tabs which will frictionally engage said housing to be selectively retained in association with said housing at a position which coincides with at least a portion of the aerial image formed by said optical system.

2. The apparatus of claim 1, wherein,
said supporting means for said transparent disc is axially adjustable along the optical axis of said optical system so as to allow repositioning of said reticle to be coincident with said aerial image.

3. The apparatus of claim 1, wherein,
said reticle is angularly adjustable relative to the optical axis of said optical system.

4. The apparatus of claim 3, wherein,
said angular adjustment of said reticle s performed by tilting of said supporting means relative to said housing.

5. The apparatus of claim 3, wherein,
said angular adjustment of said reticle is performed by tilting of said transparent disc of material relative to said supporting means.

6. The apparatus of claim 1, wherein,
said housing supports a contact lens and at least one anterior lens said contact lens including a concave surface which is positionable on the cornea of the examined eye, and said at least one anterior lens is positioned in predetermined relationship with respect to said contact lens element.

7. The apparatus of claim 1, wherein,
said housing supports at least one anterior lens and includes positioning means adapted to be positioned on the eyelids of said examined eye so as to position said at least one anterior lens in predetermined relationship to said examined eye.

8. The apparatus of claim 1, wherein,
said transparent disc of material is removable from said supporting means to allow alternate reticle scales or patterns to be used in said measurement apparatus.

9. The apparatus of claim 1, wherein,
said reticle includes a measurement scale which when position in the image plane will allow quantitative measurement of interior portions of the eye by measurement of structures on the formed image using said scale.

10. An indirect ophthalmoscopy lens for examination of the fundus of an eye using a biomicroscope comprising,
a first housing having an optical system including an imaging lens, said housing being positioned relative to the eye of a patent whereby said imaging lens will form an aerial image of a portion of the eye which can be viewed by means of a biomicroscope,
a removable reticle having means for movably positioning said reticle at a selective location relative to said imaging lens in association with said housing, said means for movably positioning said reticle allowing the distance between said reticle and said imaging lens to be adjusted, or the angular orientation of said reticle to be adjusted, or both, so as to position said reticle coincident with at least a portion of the plane of said aerial image.

11. The apparatus of claim 10, wherein,
said reticle includes a measurement scale which when positioned in said image plane will allow quantitative measurement of interior portions of the eye by measurement of structures on the formed image using said scale.

12. The apparatus of claim 10, wherein,
said means for movably positioning said reticle includes a second housing having outwardly extending yieldable tabs adapted to be received in frictional coupling relation with a surface of said first housing, said second housing being movable in axial and angular directions with respect to said imaging lens.

13. The apparatus of claim 10, wherein,
said means for movably positioning said reticle includes a second housing fixed with respect to said first housing in which said reticle is movable in axial and angular directions relative to the optical axis of said imaging lens.

14. The apparatus of claim 10, wherein,
said reticle is supported within a second housing which is selectively removable from said first housing.

15. The apparatus of claim 14, wherein,
said reticle is removable from said second housing to allow alternate reticle scales or patterns to be used in said second housing.

* * * * *